(12) United States Patent
McCullough et al.

(10) Patent No.: US 11,590,294 B2
(45) Date of Patent: Feb. 28, 2023

(54) SYRINGE ASSEMBLY FOR A DRUG DELIVERY DEVICE AND METHOD OF ASSEMBLY

(71) Applicant: AMGEN INC., Thousand Oaks, CA (US)

(72) Inventors: Adam B. McCullough, Westlake Village, CA (US); Hans Stenberg Knudsen, Vaerloese (DK); Rasmus Øhlenschlæger, Copenhagen (DK)

(73) Assignee: AMGEN INC., Thousand Oaks, CA (US)

( * ) Notice: Subject to any disclaimer, the term of this patent is extended or adjusted under 35 U.S.C. 154(b) by 207 days.

(21) Appl. No.: 16/609,483

(22) PCT Filed: Jun. 1, 2018

(86) PCT No.: PCT/US2018/035534
§ 371 (c)(1),
(2) Date: Oct. 30, 2019

(87) PCT Pub. No.: WO2018/226515
PCT Pub. Date: Dec. 13, 2018

(65) Prior Publication Data
US 2020/0197628 A1    Jun. 25, 2020

Related U.S. Application Data

(60) Provisional application No. 62/517,017, filed on Jun. 8, 2017.

(51) Int. Cl.
*A61M 5/34* (2006.01)
*A61M 5/31* (2006.01)
(Continued)

(52) U.S. Cl.
CPC .............. *A61M 5/34* (2013.01); *A61M 5/3129* (2013.01); *A61M 5/31511* (2013.01);
(Continued)

(58) Field of Classification Search
CPC .................. A61M 5/34; A61M 5/3129; A61M 5/31511; A61M 5/3293;
(Continued)

(56) References Cited

U.S. PATENT DOCUMENTS 2,545,115 A     3/1951  Son
3,994,295 A    11/1976  Wulff
(Continued)

FOREIGN PATENT DOCUMENTS

DE          287094 C      1/1915
WO     WO-9215345 A1 *   9/1992    .............. A61M 5/19
WO     WO-2018060027 A1   4/2018

OTHER PUBLICATIONS

International Search Report and Written Opinion of PCT/US2018/035534, dated Sep. 24, 2018.

*Primary Examiner* — Theodore J Stigell
*Assistant Examiner* — Rachel T. Smith
(74) *Attorney, Agent, or Firm* — Marshall, Gerstein & Borun LLP

(57) ABSTRACT

A syringe assembly for a drug delivery device. The syringe assembly includes a syringe barrel having a proximal end, a distal end, and a longitudinal axis. A needle assembly is operatively coupled to the syringe barrel and includes a needle hub and a needle attached to the needle hub. A flexible connection is disposed between the syringe barrel and the needle hub and forms a fluid pathway between the syringe barrel and the needle. The flexible connection enables the needle assembly to be moveable from a filling position, in which a longitudinal axis of the needle assembly (Continued)

is parallel to a longitudinal axis of the syringe barrel, to an assembled position, in which the longitudinal axis of the needle assembly is not parallel to the longitudinal axis of the syringe barrel.

15 Claims, 4 Drawing Sheets

(51) Int. Cl.
    *A61M 5/315*     (2006.01)
    *A61M 5/32*     (2006.01)

(52) U.S. Cl.
    CPC ............. *A61M 5/3293* (2013.01); *A61M 2005/3115* (2013.01); *A61M 2005/323* (2013.01); *A61M 2005/341* (2013.01)

(58) Field of Classification Search
    CPC .... A61M 2005/3115; A61M 2005/323; A61M 2005/341; A61M 5/14248; A61M 5/281; A61M 5/1454; A61M 2005/1581; A61M 2005/3114; A61M 5/1452
    See application file for complete search history.

(56) References Cited

U.S. PATENT DOCUMENTS

| | | | | |
|---|---|---|---|---|
| 5,405,330 | A | * | 4/1995 | Zunitch ................... A61M 5/34 604/272 |
| 2013/0041241 | A1 | * | 2/2013 | Felts ....................... C23C 16/52 604/199 |
| 2013/0131589 | A1 | | 5/2013 | Mudd et al. |
| 2014/0194854 | A1 | | 7/2014 | Tsals |
| 2016/0324455 | A1 | * | 11/2016 | Crosby ............ A61B 5/150022 |

* cited by examiner

SYRINGE ASSEMBLY FOR A DRUG DELIVERY DEVICE AND METHOD OF ASSEMBLY

CROSS-REFERENCE TO RELATED APPLICATION

This is the United States National Phase of PCT/US18/35534, filed Jun. 1, 2018, which claims the priority benefit of U.S. Provisional Patent Application No. 62/517,017, filed Jun. 8, 2017, the entire contents of each of which are hereby incorporated herein by reference.

FIELD OF THE DISCLOSURE

The present disclosure generally relates to drug delivery devices and, more particularly, a syringe assembly for a drug delivery device having a flexible needle connection to help facilitate filling and assembly of the drug delivery device.

BACKGROUND

Drug delivery devices, such as auto-injectors and on-body injectors, may be temporarily held against or attached to a patient to deliver a drug via an injection needle or some other means over some period of time. The injector may be placed against the tissue of the patient's abdomen, thigh, arm, or some other portion of the patient's body. In some cases, an on-body injector drug delivery device may be worn by the patient for several minutes or hours while the drug is injected. In other cases, the drug delivery device, such as an auto-injector, is temporarily in contact with the patient to inject the drug or medicament.

Some drug delivery devices include a syringe with medicament to be injected. Typically, the syringes are pre-filled with the medicament before assembly into the drug delivery device for various reasons. In one example, the syringe is pre-filled before assembly because existing filling equipment is only capable of filling the syringes in a pre-assembled configuration. For example, some existing processing and filling equipment requires a linear configuration of a syringe needle and barrel of the syringe during processing. Said another way, the syringe needle and barrel of the syringe must be coaxial during many conventional filling processes. However, some conventional syringe assemblies have one or more of a subtle non-linear or asymmetrical configuration during the filling process, interfering with or making the filling process unfeasible. In addition, while other syringe assemblies may be capable of maintaining a linear configuration during the filling process, they are not capable of being easily manipulated out of the linear configuration, e.g., the required filling position, for assembly into various ergonomic designs and shapes of many drug delivery devices.

SUMMARY

In accordance with a first aspect, a drug delivery device comprises a housing having an actuating mechanism and a syringe assembly disposed within the housing and operatively coupled to the actuating mechanism. The syringe assembly includes a syringe barrel having a proximal end, a distal end, and a longitudinal axis, and a needle assembly operatively coupled to the syringe barrel. The needle assembly has a needle hub and a needle attached to the needle hub. The syringe assembly further includes a flexible connection disposed between the syringe barrel and the needle hub. The flexible connection has a proximal end and a distal end, with the proximal end being coupled to the distal end of the syringe barrel and the distal end being coupled to the needle hub. In addition, the flexible connection forms a fluid pathway between the syringe barrel and the needle. So configured, the flexible connection enables the needle and needle hub to be moveable from a filling position, in which a longitudinal axis of the needle and the needle hub is parallel to the longitudinal axis of the syringe barrel, to one or more of an assembled position or an actuated position, in which the longitudinal axis of the needle and needle hub is not parallel to the longitudinal axis of the syringe barrel. This allows the needle assembly to be disposed in various positions within the housing during one or more of assembly, use, preparation or actuation of the drug delivery device.

In accordance with a second aspect, a syringe assembly for a drug delivery device comprises a syringe barrel having a longitudinal axis and a needle assembly operatively coupled to the syringe barrel. The needle assembly has a needle hub and a needle attached to the needle hub, and the needle is stationary relative to the needle hub. The syringe assembly further comprises a flexible connection disposed between the syringe barrel and the needle assembly. The flexible connection has a proximal end and a distal end, and the proximal end is coupled to the syringe barrel and the distal end is coupled to the needle hub. So configured, the flexible connection enables the needle assembly to be moveable from a filling position to one or more of an assembled position or an actuated position, the filling position a position in which a longitudinal axis of the needle assembly is parallel to a longitudinal axis of the syringe barrel, and the assembled position and the actuated position are positions in which the longitudinal axis of the needle assembly is not parallel to the longitudinal axis of the syringe barrel. This allows the needle to be disposed in various positions within the drug delivery device during one or more of assembly into, actuation of, or use of the drug delivery device.

In accordance with yet another aspect, a method of assembling a drug delivery device comprises maintaining a filling position of a syringe assembly during a processing state, the filling position a position in which a longitudinal axis of a needle assembly of the syringe assembly is parallel to a longitudinal axis of a syringe barrel of the syringe assembly. The method further comprises moving the needle assembly from the filling position to an assembled position within the drug delivery device by a flexible connection, the flexible connection disposed between and coupled to the syringe barrel and the needle assembly, and the assembled position a position in which the longitudinal axis of the needle assembly is not parallel to the longitudinal axis of the syringe barrel.

In accordance with yet another aspect, a syringe assembly for a drug delivery device includes a syringe barrel having a longitudinal axis and a needle assembly operatively coupled to the syringe barrel. The needle assembly has a needle operatively coupled to the syringe barrel. A flexible connection is disposed between the syringe barrel and the needle assembly and includes one or more of a cylindrical or spherical portion coupled to the syringe barrel and the needle. The flexible connection enables the needle assembly to be moveable from a filling position to one or more of an assembled position or an actuated position. The filling position is a position in which a longitudinal axis of the needle assembly is parallel to a longitudinal axis of the syringe barrel, and the assembled position and the actuated position are positions in which the longitudinal axis of the needle assembly is not parallel to the longitudinal axis of the syringe barrel. So configured, the needle is allowed to be disposed in various positions within the drug delivery device during one or more of assembly, actuation, or use of the drug delivery.

In accordance with still yet another aspect, a syringe assembly for a drug delivery device comprises a syringe barrel having a longitudinal axis and a needle assembly operatively coupled to the syringe barrel. The needle assembly has a needle hub and a needle attached to the needle hub. A flexible connection is disposed between the syringe barrel and the needle assembly, the flexible connection including one or more of: (1) a proximal end coupled to the syringe barrel and a distal end coupled to a needle hub, (2) a tube, or (3) one or more of a cylindrical or spherical portion. So configured, the flexible connection enables the needle assembly to be moveable from a filling position to one or more of an assembled position or an actuated position. The filling position is a position in which a longitudinal axis of the needle assembly is parallel to a longitudinal axis of the syringe barrel. The assembled position and the actuated position are positions in which the longitudinal axis of the needle assembly is one or more of parallel to the longitudinal axis of the syringe barrel or not parallel to the longitudinal axis of the syringe barrel. So configured, the needle is allowed to be disposed in various positions within the drug delivery device during one or more of assembly, actuation, or use of the drug delivery device.

In further accordance with any one or more of the foregoing first and second aspects and method, the syringe assembly for a drug delivery device and method may include any one or more of the following forms or method steps.

In one form, the needle may be stationary relative to the needle hub, and the syringe barrel may be stationary relative to the needle. In addition, the needle, the needle hub, the flexible connection, and the syringe barrel may be coaxial in the filling position. Further, the needle and the needle hub may be coaxial and the needle hub and the syringe barrel may be non-coaxial in one or more of the assembled position or the actuated position. Still further, the longitudinal axis of the needle and the needle hub may be perpendicular to the longitudinal axis of the syringe barrel in one or more of the assembled position or the actuated position. In addition, the longitudinal axis of the needle and the needle hub may be disposed at an angle that is not parallel to the longitudinal axis of the syringe barrel in one or more of the assembled position or the actuated position.

In another form, the syringe barrel may include a projection disposed at the distal end of the syringe barrel, and the projection may have a width that is less than a width of the syringe barrel. In addition, the flexible connection may include a width that is one or more of substantially the same or less than a width of the syringe barrel and a length that is less than a length of the syringe barrel. Further, the flexible connection may be moveable at any point along the length or the width of the flexible connection, which may allow movement of the needle without movement of the syringe barrel.

In yet other forms, the needle hub may further include a proximal surface that is coupled to the distal end of the flexible connection and a distal surface that is coupled to the needle. Further, the proximal surface may have a width that is greater than a width of the distal surface, such that the width of the needle hub decreases in a direction from the proximal surface to the distal surface.

In yet another form, the syringe assembly may further comprise one or more rigid connections separate from or integrated with the flexible connection. In one example, the rigid connection may have a proximal portion coupled to the distal end of the syringe barrel and a distal portion coupled to the needle hub. In addition, the rigid connection may further include a body having a proximal leg downwardly and outwardly extending from the body and a distal leg downwardly and outwardly extending from the body. Further, each of the distal and proximal legs may have a portion that fits within a corresponding aperture disposed in the distal end of the syringe barrel and the needle hub, respectively, to secure the rigid connection to the syringe assembly. Still further, the rigid connection may ensure the longitudinal axis of the needle and needle hub is parallel to a longitudinal axis of the syringe barrel in the filling position.

In yet other forms, the syringe barrel may include one or more of a cylindrical or spherical member having one or more of a socket or an opening, and one or more of the cylindrical or spherical portion of the flexible connection is disposed within the cylindrical or spherical member of the syringe barrel. This allows the needle to be rotated between the filling position and or more of the assembled or actuated positions. In addition, the syringe assembly may further include one of an o-ring or seal disposed between one or more of the cylindrical or spherical member of the syringe barrel and one or more of the cylindrical or spherical portion of the flexible connection.

In one form of the method, the method may further comprise filling the syringe barrel of the syringe assembly with medicament in the filling position. In addition, the method may further comprise forming a fluid pathway between the syringe barrel and the needle assembly by the flexible connection.

In another form of the method, maintaining a filling position of a syringe assembly during a processing state may comprise maintaining a filling position of a syringe assembly by a rigid connection separate from the flexible connection, the rigid connection having a proximal portion coupled to the syringe barrel and a distal portion coupled to a needle hub of the needle assembly.

In yet another form of the method, moving the needle assembly from the filling position to an assembled position by a flexible connection may comprise moving the flexible connection disposed between the syringe barrel and the needle hub, such that the needle assembly, the flexible connection, and the syringe barrel are non-coaxial. Alternatively and/or additionally, moving the needle assembly from the filling position to the assembled position by a flexible connection may comprise moving the needle assembly to a position perpendicular to a longitudinal axis of the syringe barrel.

In yet another form of the method, the method may further comprise maintaining alignment of the needle assembly with the syringe barrel in the filling position by a rigid connection disposed between the needle assembly and the syringe barrel, the rigid connection separate from the flexible connection. In another example, the method may further comprise disposing the syringe assembly into the body of the drug delivery device.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the example embodiments, except as may be explicitly delineated in the corresponding written description. Also, none of the drawings is necessarily to scale.

DETAILED DESCRIPTION

A drug delivery device, such as an auto-injector or a wearable (e.g., on-body) injector, having a new syringe assembly is disclosed. The drug delivery device includes a housing having an actuating mechanism and the syringe assembly is disposed within the housing and operatively coupled to the actuating mechanism. The syringe assembly includes a syringe barrel having a proximal end, a distal end, and a longitudinal axis. A needle assembly is operatively coupled to the syringe barrel and includes a needle hub and a needle attached to the needle hub. A flexible connection is disposed between the syringe barrel and the needle hub and includes a proximal end and a distal end. The proximal end of the flexible connection is coupled to the distal end of the syringe barrel and the distal end of the flexible connection is coupled to the needle hub. So configured, the flexible connection enables the needle assembly to be moveable from a filling position, in which a longitudinal axis of the needle assembly is parallel to a longitudinal axis of the syringe barrel, to an assembled position, in which the longitudinal axis of the needle assembly is not parallel to the longitudinal axis of the syringe barrel. As a result, the needle of the pre-filled syringe assembly is able to be disposed in many positions within the drug delivery device to accommodate various form factors (e.g., ergonomic shapes and sizes) of the drug delivery devices.

Figure 1:
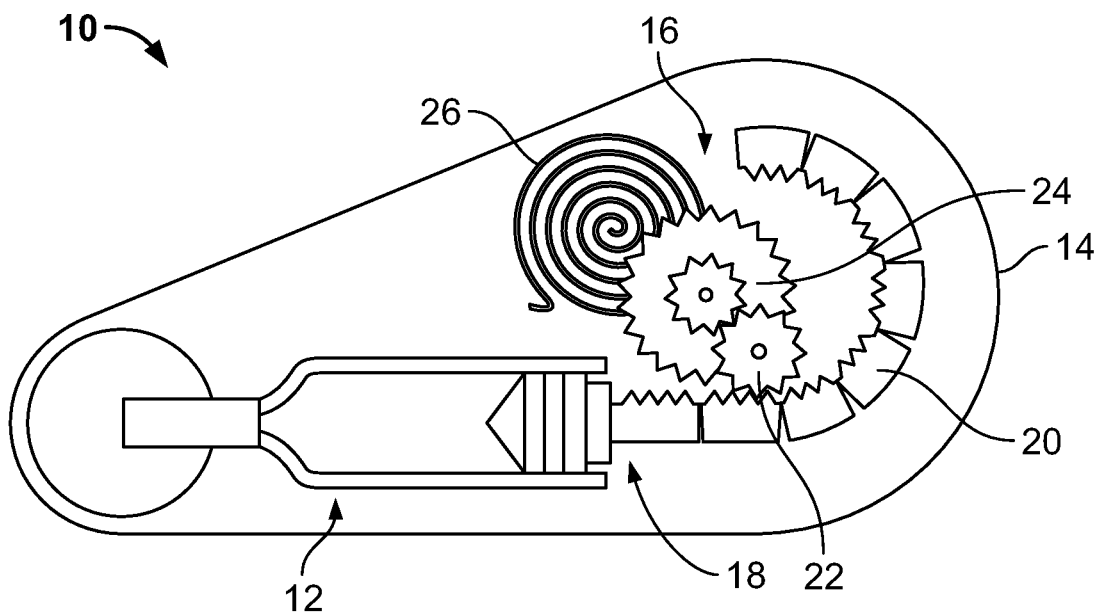
FIG. 1 is a top sectional view of one embodiment of a drug delivery device having a syringe assembly in accordance with the teachings of the present disclosure.

More specifically, and referring now to FIG. 1, one example of a drug delivery device 10 having a syringe assembly 12 according to the present disclosure is depicted. In at least one example, the drug delivery device 10 may be configured as a drug delivery device, such as an auto-injector or on-body injector, that may be placed into contact with a patient's tissue (e.g., the patient's skin) to administer delivery of a drug treatment. Upon actuation, for example, the drug delivery device 10 may deliver an injection of a fixed dose of a drug. The drug delivery device 10 may be intended for self-administration by the patient, but may also be used by a caregiver or a formally trained healthcare provider.

The drug delivery device may include a housing 14 having an actuating mechanism 16. The actuating mechanism 16 may be coupled to the syringe assembly 12 by a plunger 18 disposed within the syringe assembly 12. In one example, the plunger 18 includes a curved shaft 20, which may be sectioned for flexibility and possess a plurality of gear teeth, as depicted in FIG. 1. A nut gear 22 with corresponding gear teeth may be disposed on or in meshing engagement with the gear teeth of the curved shaft 20 of the plunger 18. The actuating mechanism 16 may include another gear, such as a spring case gear 24 also equipped with gear teeth, which are meshingly engaged with the teeth of the nut gear 22 to drive the nut gear 22. The actuating mechanism 16 may further include a watch spring 26 that is coupled to the spring case gear 24 and drives the spring case gear 24. When the nut gear 22 is rotated by the spring case gear 24 driven by the watch spring 26, the meshed teeth connection drives the plunger rod or shaft 20 into the syringe assembly 12.

Figure 2:
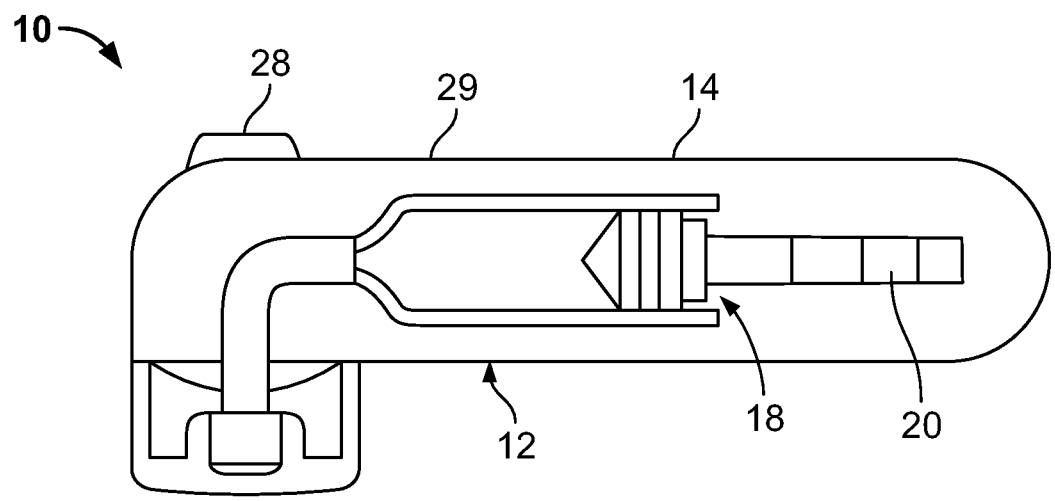
FIG. 2 is a side sectional view of the drug delivery device of FIG. 1.

Referring now to FIG. 2, a side perspective view of the drug delivery device 10 is depicted. The syringe assembly 12 is in an assembled configuration within the housing 14, as explained more below. In addition, an actuating button 28 is disposed on an outside surface 29 of the housing 14. In this way, the actuating button 28 can be easily actuated to move the plunger 18 coupled to the actuating mechanism 16 (FIG. 1) and inject the medicament disposed within the syringe assembly 12.

As depicted in both FIGS. 1 and 2, the drug delivery device 10 may take the form of a pod shaped device. This form factor enables a user, such as a patient, to easily grip the housing 14 of the pod device the palm of in his or her hand to prepare the drug delivery device 10 for administration. The smooth, rounded, and ergonomic design helps patients more easily handle injection instead of using a conventional syringe delivery mechanism, which can be difficult to handle and/or create anxiety for some patients.

While the drug delivery device 10 of FIGS. 1 and 2 is depicted as the rounded, pod-shaped device, one of ordinary skill in the art will appreciate that the drug delivery device 10 may alternatively or additionally take the shape of various other forms and still fall within the scope of present disclosure. For example, the drug delivery device 10 may be one or more of semi-cylindrical, cylindrical, semi-circular, circular, semi-spherical, spherical or any other form that is still able to accommodate the new syringe assembly 12 of the present disclosure, as explained more below, and still fall within the scope of the present disclosure.

Figure 3A:
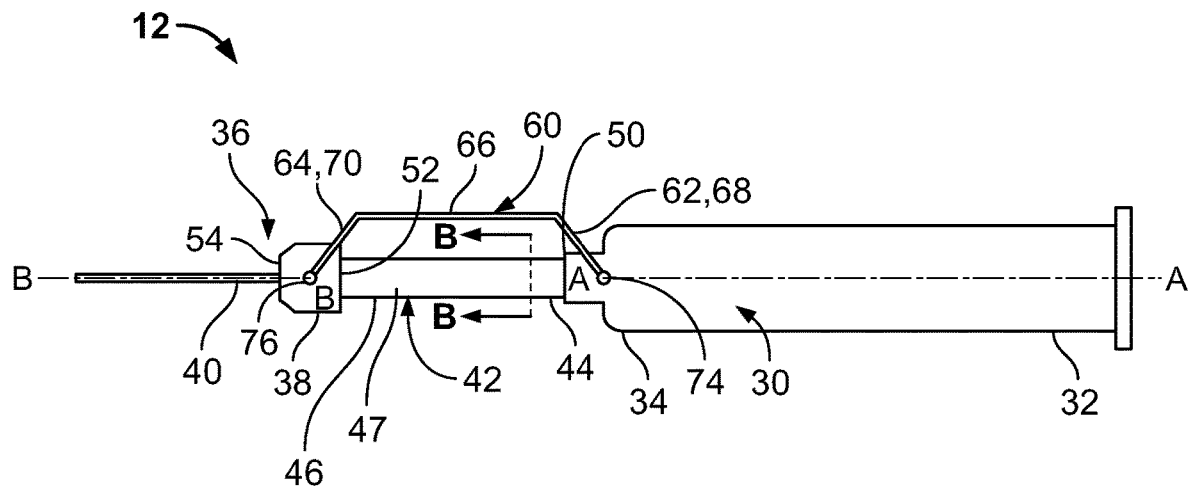
FIG. 3A is side view of the syringe assembly according to one aspect of the present disclosure.

Referring now to FIG. 3A, the syringe assembly 12 of the present disclosure is depicted in a filling position. In this position, the syringe assembly 12 is able to be filled with medicament by filling and/or processing equipment, as further explained below. In addition, in the filling position, the syringe assembly 12 is not disposed within the housing 14 of the drug delivery device 10. Rather, it is in an assembled position (see, e.g., FIG. 2) that the syringe assembly 12 is disposed within the housing 14 and operatively coupled to the actuating mechanism 16, as described above.

As depicted in FIG. 3A, the syringe assembly 12 includes a syringe barrel 30 having a proximal end 32, a distal end 34, and a longitudinal axis A. The syringe barrel 30 receives medicament from filling and/or processing equipment in the filling position.

The syringe assembly 12 further includes a needle assembly 36 operatively coupled to the syringe barrel 30. In one example, the needle assembly 36 may include a needle hub 38 and a needle 40 attached to the needle hub 38, as depicted in FIG. 3A. The needle assembly 36, including the needle hub 38 and the needle 40, has a longitudinal axis B. In one example, the needle 40 is stationary relative to the needle hub 38. Said another way, the needle 40 does not move relative to the needle hub 38, such that the needle nub 38 and the needle 40 are always disposed parallel to each other along the longitudinal axis B, e.g., along the same axis.

A flexible connection 42 is disposed between the needle assembly 36 and the syringe barrel 30. More specifically, and in one example, the flexible connection 42 may have a proximal end 44 and a distal end 46. The proximal end 44 is coupled to the distal end 34 of the syringe barrel 30. The distal end 46 of the flexible connection 42 is coupled to the needle hub 38. In one example, the flexible connection 42 forms a fluid pathway 47 between the syringe barrel 30 and the needle 40. So configured, the flexible connection 42 enables the needle and needle hub 38 to be moveable from a filling position (FIG. 3A), in which a longitudinal axis B of the needle 40 and the needle hub 38 is parallel to a longitudinal axis A of the syringe barrel 30, to one or more of an assembled position or an actuated position (e.g., FIG. 4). The assembled position and the actuated position are positions in which the longitudinal axis B of the needle 40 and needle hub 38 is not parallel to the longitudinal axis A of the syringe barrel 30.

Figure 3B:
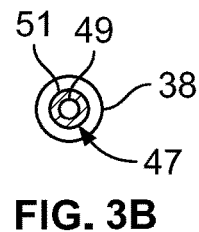
FIG. 3B is a cross-sectional view of a portion of the syringe assembly of FIG. 3A taken along the line B-B of FIG. 3A.

In addition, and as depicted in FIG. 3B, the flexible connection 42 may include a flexible tube having at least two layers, such as an inner layer 49 and an outer layer 51. The tube may be coextruded, and the inner layer 49 may include material selected for drug product contact, such as bromobutyl rubber. The outer layer 51 may include material selected for vapor barrier properties. In another example, the outer layer 51 may include a Teflon heat-shrink sleeve. More specifically, in one example, the heat-shrink sleeve may be applied to the inner layer 49 to form an outer layer 51 of the flexible connection 42. In this example, the tube may include one or more of a shape memory alloy or nitinol. Alternatively, the flexible connection 42 may include a flexible tube having only a single layer. In this example, the flexible tube may comprise stainless steel.

As depicted in FIG. 3A, the needle 40, the needle hub 38, the flexible connection 42, and the syringe barrel 30 are coaxial in the filling position. Said another way, the needle assembly 36, the flexible connection 42, and the syringe barrel 30 are coaxial in the filling position. In other words, the needle assembly 36, the flexible connection 42, and the syringe barrel 30 are handled as a linear assembly or configuration, all disposed along the same axis, in the filling position. In this way, the existing filling and/or processing equipment requiring the syringe assembly to be in a linear configuration, for example, may be effectively used with the new syringe assembly 12. Such equipment can typically include a cradle or holder designed to receive and hold one or more syringes in an upright vertical configuration for filling medicament under the force of gravity into the syringe barrel 30 through the open proximal end 32.

Figure 4:
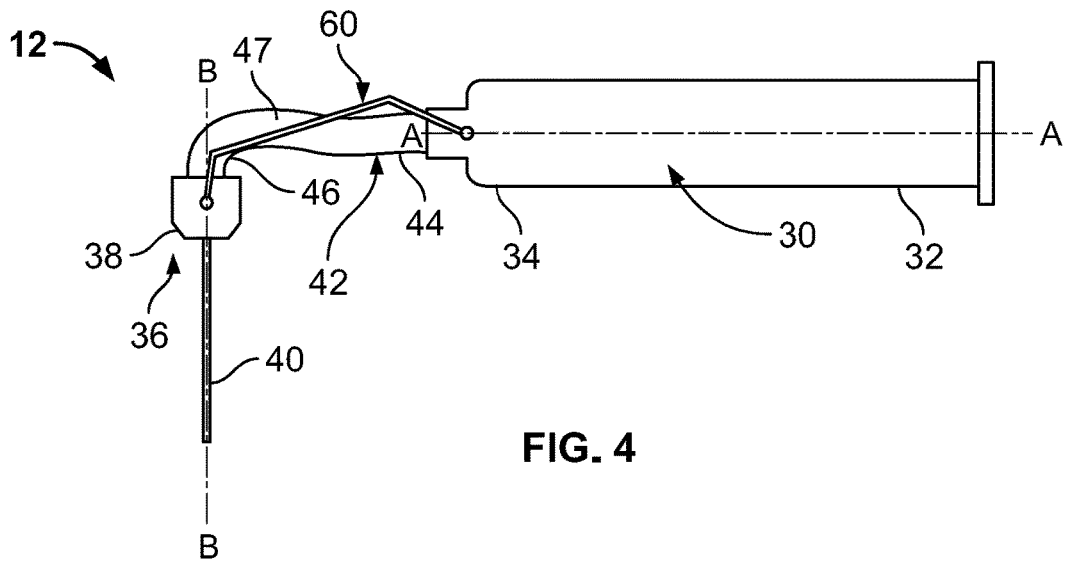
FIG. 4 is another side view of the syringe assembly according to another aspect of the present disclosure.

Referring now to FIG. 4, the syringe assembly 12 is depicted in an assembled position. In one example, and as noted, the assembled position is a position in which the syringe assembly 12 is disposed within the housing 14 of the drug delivery device 10 after the barrel 30 of the syringe assembly 12 is filled in one or more of a filling state and/or a processing state. In the assembled position, the longitudinal axis B of the needle assembly 36 is not parallel to the longitudinal axis A of the syringe barrel 30. In the assembled position, the needle 40 and the needle hub 38 are still coaxial, as they are stationary relative to each other, but the needle hub 38 and the syringe barrel 30, for example, are non-coaxial in the assembled position. Said another way, the needle assembly 36 and the syringe barrel 30 are non-coaxial in the assembled position. In another example, the needle assembly 36 and the syringe barrel 30 may be coaxial in one or more of the assembled position or an actuated position during operation of the drug delivery device, as explained more below.

In one example, and as depicted in FIG. 4, the longitudinal axis B of the needle 40 and the needle hub 38 may be perpendicular to the longitudinal axis A of the syringe barrel 30 in the assembled position. Alternatively, the longitudinal axis B of the needle 40 and the needle hub 38 may be disposed at an angle from the longitudinal axis A of the syringe barrel 30 that is less than 90 degrees and greater than 0 degrees. Still further, the longitudinal axis B of the needle 40 and the needle hub 38 may be disposed at an angle from the longitudinal axis A of the syringe barrel 30 that is less than 180 degrees and greater than 0 degrees. Said another way, the longitudinal axis B of the needle 40 and the needle hub 38 may be disposed at an angle that is not parallel to the longitudinal axis A of the syringe barrel 30 in the assembled position. The particular angle will at least partly be dictated by the final form factor of the drug delivery device 10 being used. In any case, in the assembled position the flexible connection 42 enables the needle assembly 36 to be moved from the linear, filling position (e.g., FIG. 3) to any other position with the drug delivery device to accommodate many shapes and sizes and designs of various drug delivery devices. In yet another example, the assembled position may be a position in which the longitudinal axis B of the needle 40 is parallel to the longitudinal axis A of the syringe barrel.

While FIG. 4 depicts the syringe assembly 12 in the assembled position, one of ordinary skill in the art will appreciate that during use of the drug delivery device 10, for example, or any other drug delivery device in which the syringe assembly 12 may be disposed, the actuated position may include many of the same if not all of the features of the assembled position. Said another way, during actuation of the drug delivery device 10 or the actuated position, the longitudinal axis B of the needle assembly 36 is not parallel to the longitudinal axis A of the syringe barrel 30. In addition, in the actuated position, the needle 40 and the needle hub 38 are still coaxial, as they are stationary relative to each other, but the needle hub 38 and the syringe barrel 30, for example, are non-coaxial. Said another way, the needle assembly 36 and the syringe barrel 30 may also be non-coaxial in the actuated position.

Further, and again like the assembled position, the longitudinal axis B of the needle 40 and the needle hub 38 may be perpendicular to the longitudinal axis A of the syringe barrel 30 in the actuated position. In yet another example, the actuated position may be a position in which the longitudinal axis B of the needle 40 is parallel to the longitudinal axis A of the syringe barrel. Alternatively, the longitudinal axis B of the needle 40 and the needle hub 38 may be disposed at an angle from the longitudinal axis A of the syringe barrel 30 that is less than 90 degrees and greater than 0 degrees in the actuated position. Still further, the longitudinal axis B of the needle 40 and the needle hub 38 may be disposed at an angle from the longitudinal axis A of the syringe barrel 30 that is less than 180 degrees and greater than 0 degrees in the actuated position. Said another way, the longitudinal axis B of the needle 40 and the needle hub 38 may be disposed at an angle that is not parallel to the longitudinal axis A of the syringe barrel 30 in the actuated position. The particular angle will at least partly be dictated by the final form factor of the drug delivery device 10 being used. This enables the needle assembly 36 to be moved from the linear, filling position (e.g., FIG. 3A) to any other position, such as the assembled position (e.g., FIG. 4) and the actuated position, within the drug delivery device to accommodate many shapes and sizes and designs of various insertion and/or retraction mechanisms and/or drug delivery devices.

In another example, and referring back to FIG. 3A, the syringe barrel 30 may include a projection 50 disposed at the distal end 34 of the syringe barrel 30. The projection 50 may have a width that is less than or the same as a width of the syringe barrel 30. In addition, the flexible connection 42 may include a width that is one or more of substantially the same or less than the width of the projection 50 of the syringe barrel 30. Still further, the flexible connection 42 may include a length that is less than a length of the syringe barrel 30. The flexible connection 42 is moveable at any point along the length or the width of the flexible connection 42. In some examples, the flexible connection 42 allows movement of the needle 40 (and the needle hub 38) without movement of the syringe barrel 30, providing an advantage for some needle insertion and/or retraction mechanisms in various drug delivery devices.

Still further, in other examples, an alternative to the flexible connection 42 could be a mechanical joint. The mechanical joint could include a valve, which may take the form of a spherical ball valve, in one example. More specifically, the spherical ball valve may be disposed between the pair of tubular conduits, which connect to the hub and barrel, respectively. So configured, components of the ball valve can rotate relative to each other, thereby allowing pivoting of the tubular conduits to facilitate movement of the needle from the filling position (FIG. 3A) to the example assembled or actuated position (FIG. 4). In the assembled or actuated position, the ball valve could occupy an open position enabling fluid communication between the barrel and the needle. In one example, the presence of the valve, such as the spherical ball valve, adjacent to the syringe barrel enables a wider variety of materials to be used for the flexible connection 42. This is at least because a container closure would occur at the valve and the flexible connection 42 would then only be subject to short term drug or medicament contact if the valve was opened at administration and not assembly, for example.

As one of ordinary skill in the art will understand, the flexible connection 42 may take the form of various other shapes and sizes and still fall within the scope of the present disclosure. In one example, the flexible connection 42 may include various other components. In another example, the flexible connection 42 may alternatively and/or additionally be semi-cylindrical, semi-circular, circular, spherical or semi-spherical in shape and still fall within the scope of the present disclosure.

As depicted in FIG. 3A, the needle hub 38 may further include a proximal surface 52 that is coupled to the distal end 46 of the flexible connection 42 and a distal surface 54 that is coupled to the needle 40. The proximal surface 52 may have a width that is greater than a width of the distal surface 54 of the needle hub 38, such that the needle hub 38 width one or more of decreases or narrows in a direction from the proximal surface 52 to the distal surface 54 of the needle hub 38. Other configurations are possible.

In some examples, a rigid connection 60 separate from the flexible connection 42 may be further included in the syringe assembly 12. The rigid connection 60 may have a proximal portion 62 coupled to the distal end 34 of the syringe barrel 30 and a distal portion 64 coupled to the needle hub 38. Additionally and/or alternatively, the rigid connection 60 may further include a body 66 having a proximal leg 68 downwardly and outwardly extending from the body 66 and a distal leg 70 downwardly and outwardly extending from the body 66. Each of the distal and proximal legs 68, 70 may have a tab or pin that fits within a corresponding aperture in the hub 38 and barrel 30, respectively. More specifically, the distal end 34 of the syringe barrel 30 may include an aperture 74 for receiving a tab or pin protruding from the proximal leg 68 of the rigid connection 60. In a similar manner, the needle hub 38 may also include an aperture 76 for receiving a tab or pin protruding from the distal leg 70 of the rigid connection 60. So configured, the rigid connection 60 ensures the longitudinal axis B of the needle 40 and needle hub 38 is parallel to a longitudinal axis A of the syringe barrel 30 in the filling position. In this example, the body 66 of the rigid connection 60 may be a wire-like member, a hinged pin member, a hinged plate member, or some other similarly suitable structure, which may be made of a metal, a plastic, a composite, or any other material having a suitable material strength.

In another example, the rigid connection 60 may include a plurality of rigid connections. For example, there may alternatively or additionally be another rigid connection (not shown) disposed on another side of the syringe assembly 12 opposite the side the rigid connection 60 is disposed in FIGS. 3A, 3B, and 4. The additional rigid connection may likewise include two legs, one of which is disposed within a portion, such as another aperture, of the syringe barrel 30 on the other side of the syringe barrel 30, and the other of which is disposed in another portion of the needle hub 38. In this example, the additional rigid connection or the plurality of rigid connections provide further support to the syringe assembly 12 in the filling position, further ensuring the needle assembly 36 is maintained in a linear position parallel to a longitudinal axis A of the syringe barrel 30.

Still further, in other examples, the rigid connection 60 may take the form of various other shapes and sizes and still fall within the scope of the present disclosure. For example, the rigid connection 60 may include only a single body portion having ends that are directly coupled to the syringe barrel 30 and the needle hub 38, respectively. In one example, the proximal portion 62 and the distal portion 64 of the rigid connection 60 may form a single component together with the syringe barrel 30 and the needle hub 38. Molded hinges, such as film hinges, may be used to couple the proximal portion 62 to the distal end 34 of the syringe barrel 30 and the distal portion 64 to the needle hub 38. In yet another example, any connection between the proximal portion 62 and the syringe barrel 20 and the distal portion 64 and the needle hub 38 may be one or more of broken or disconnected after filling until the time of use, preferably by a time of assembly with the drug delivery device 10.

In another example, the rigid connection 60 may include a shape memory alloy, such as a Nitinol wire or wires, or external tubing or a tube. The shape memory alloy is able to hold one position, such as a first position, during filling or processing. The shape memory alloy then "remembers" or moves to another predefined position, such as a second position, when the temperature is increased to a threshold temperature. In one example, the threshold temperature is above 15 degrees Celsius when the device is being prepared for use. In another example, the threshold temperature is above 37 degrees Celsius in response to an onboard heating control circuit.

In yet another example, an external component may be snapped onto each of the needle hub 38 and the syringe barrel 30, preferably after manufacturing of the needle hub 38 and the syringe barrel 30. More specifically, the external component may be snapped onto the needle hub 38 where the distal portion 64 of the rigid connection 60 is coupled to the needle hub 38. In a similar manner, the external component may be snapped onto the syringe barrel 30, such as the distal portion 34 of the syringe barrel, where the proximal portion 62 is coupled to the syringe barrel 30. The external components may then be snapped off each of the needle hub 38 and the syringe barrel 30 by the time of use, and preferably by the time of assembly within the drug delivery device.

In yet another example, the rigid connection 60 may include a cylindrical sleeve disposed around and about the flexible connection in the filling state. Upon movement to the assembled position, the cylindrical sleeve may be removed, for example, allowing the flexible connection to be moved, and, thus, the needle assembly to be moved to a position that is not parallel to the longitudinal axis A of the syringe barrel 30.

In one example, the flexible connection 42 may be made of one or more of a polymer or an elastomer, and can generally comprise a flexible tubing such as conventional medical grade tubing.

Figure 5:
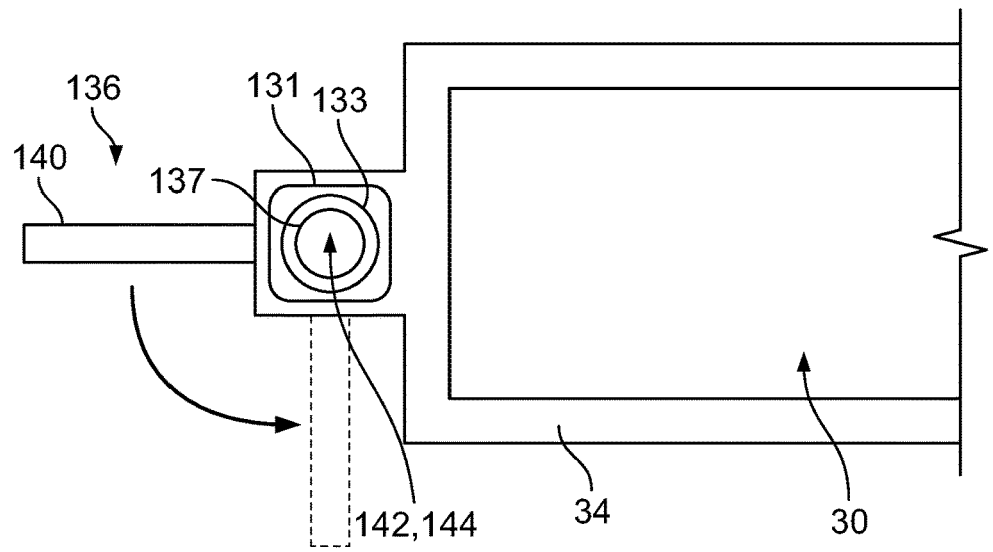
FIG. 5 is a side view of another syringe assembly according to another aspect of the aspect of the present disclosure.

Referring now to FIG. 5, another syringe assembly 112 according to another aspect of the present disclosure is depicted. The syringe assembly 112 may be disposed within the drug delivery device 10 of FIGS. 1 and 2, for example, and any other alternatively shaped, sized, operated, and/or actuated drug delivery device known to persons of ordinary skill in the art. In addition, parts of the syringe assembly 112 identical to parts of the syringe assembly 12 of FIGS. 3 and 4 include the same reference numbers as the syringe assembly 12 and are not described again here. Likewise, parts of the syringe assembly 112 different from the syringe assembly 12 of FIGS. 3 and 4 include different reference numbers and are explained more below. In particular, the syringe assembly 112 of FIG. 5 includes a flexible connection 142 that is different from the flexible connection 42 of the syringe assembly 12, as described more below.

As depicted in FIG. 5, the syringe assembly 112 includes the syringe barrel 30 having a longitudinal axis and a needle assembly 136 operatively coupled to the syringe barrel 30. The syringe barrel 30 further includes one or more of a cylindrical or spherical portion 131 disposed at the distal end 34 of the syringe barrel 30. The cylindrical or spherical portion 131 includes one or more of a socket or an opening 133. The needle assembly 136 includes a needle 140 operatively coupled to the syringe barrel 30, as explained more below. A flexible connection 142 is disposed between the syringe barrel 30 and the needle assembly 136 and includes one or more of a cylindrical or spherical member 144. The cylindrical or spherical member 144 is disposed within one or more of the socket or the opening 133 of the cylindrical or spherical portion 131 of the syringe barrel 30. In addition, an o-ring 137 or other seal may be disposed between one or more of the cylindrical or spherical member 131 of the syringe barrel 30 and one or more of the cylindrical or spherical portion 144 of the flexible connection 142.

In operation, the flexible connection 142 enables the needle assembly 136, in particular the needle 140, to be one or more of moveable or rotatable from a filling position to one or more of an assembled position or an actuated position. As described above relative to the syringe assembly 12, the filling position is a position in which a longitudinal axis of the needle assembly 136 is parallel to a longitudinal axis of the syringe barrel 30. Likewise, the assembled position and the actuated position are positions in which the longitudinal axis of the needle assembly 136 is not parallel to the longitudinal axis of the syringe barrel 30, allowing the needle to be disposed in various positions within the drug delivery device during one or more of assembly, actuation, or use of the drug delivery device. In addition, the needle 140, the flexible connection 142, and the syringe barrel 30 are coaxial in the filling position, as depicted in FIG. 5. Further, the needle 142 and the syringe barrel 30 are non-coaxial in one or more of the assembled position or the actuated position, as depicted by the dashed lines of the needle 140 of FIG. 5 that correspond to a position of the needle 140 in the assembled position, for example. Still further, the longitudinal axis of the needle 140 is perpendicular to the longitudinal axis of the syringe barrel 30 in one or more of the assembled position or the actuated position.

Referring now to FIGS. 6A-6D, another syringe assembly 212 according to another aspect of the present disclosure is depicted. The syringe assembly 212 may be disposed within the drug delivery device 10 of FIGS. 1 and 2, for example, and/or any other alternatively shaped, sized, operated, and/or actuated drug delivery device known to persons of ordinary skill in the art. In addition, parts of the syringe assembly 212 identical to parts of the syringe assembly 12 of FIGS. 3 and 4 include the same reference numbers as the syringe assembly 12 and are not described again here. Likewise, parts of the syringe assembly 212 different from the syringe assembly 12 of FIGS. 3 and 4 include different reference numbers and are explained more below. In particular, the syringe assembly 212 of FIGS. 6A-6C includes a flexible connection 242 that is different from the flexible connections 42, 142 of the syringe assemblies 12, 112, respectively, as described more below.

Figure 6A:
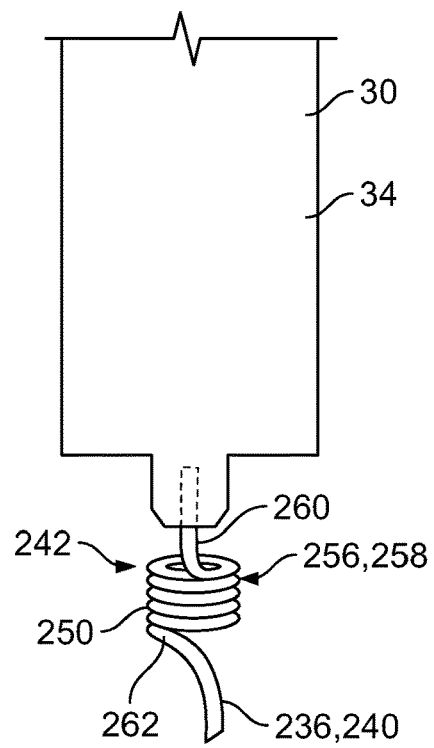
FIG. 6A is a side view of a portion of another syringe assembly according to another aspect of the present disclosure, the syringe assembly in an initial position.
Figure 6B:
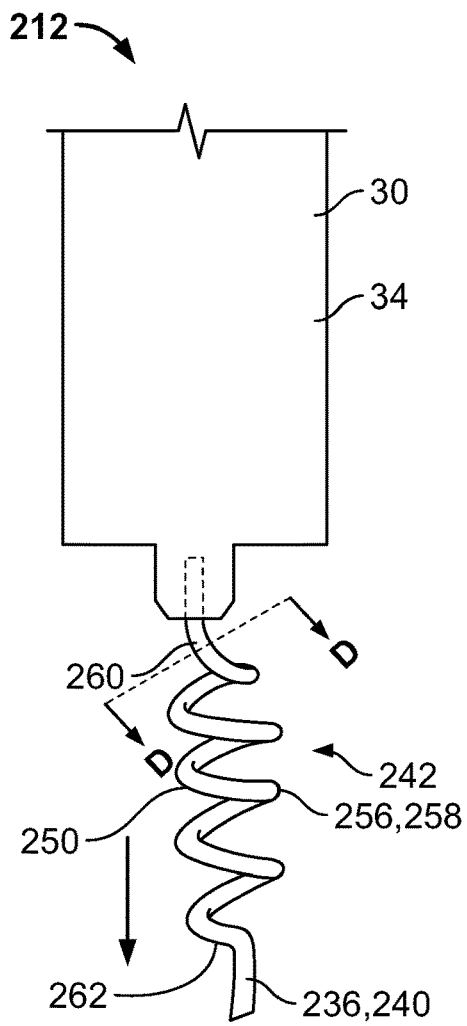
FIG. 6B is another side view of the portion of the syringe assembly of FIG. 6A, the syringe assembly in one of an assembled or actuated position.
Figure 6C:
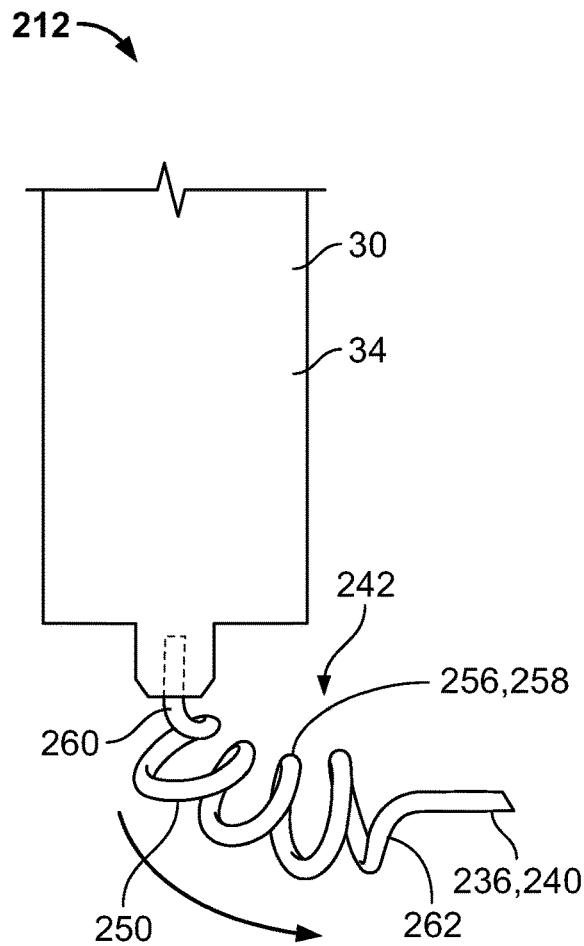
FIG. 6C is another side view of the portion of the syringe assembly of FIG. 6A, the syringe assembly in one of another assembled or actuated position.
Figure 6D:
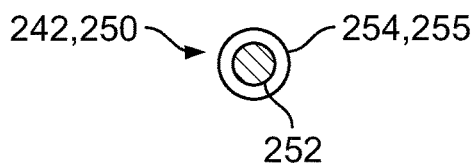
FIG. 6D is a cross-sectional view of a portion of the syringe assembly of FIG. 6B taken along the line D-D of FIG. 6B.

As depicted in FIG. 6A, the syringe assembly 212 includes the syringe barrel 30 having a longitudinal axis. A needle assembly 236 is operatively coupled to the syringe barrel and includes a needle 240. A flexible connection 242 is disposed between the syringe barrel 30 and the needle assembly 236 and includes a tube 250. The tube 250 may include at least two layers comprising an inner layer 252 and an outer layer 254, as depicted in FIG. 6D. In one example, the flexible connection 242 and needle 240 may be formed as a single piece construction, with no other connection or coupling member needed between the flexible connection 242 and the needle assembly 236 or needle 240.

In operation, the flexible connection 242 enables the needle assembly 236 to be moveable from a filling position to one or more of an assembled position or an actuated position. As described above relative to the syringe assemblies 12, 112, the filling position is a position in which a longitudinal axis of the needle assembly 236 is parallel to a longitudinal axis of the syringe barrel 30, as depicted in FIG. 6A. In addition, in this example, the assembled position and the actuated position are positions in which the longitudinal axis of the needle assembly 236 is one or more of parallel to the longitudinal axis of the syringe barrel 30, as depicted in FIG. 6B, or not parallel to the longitudinal axis of the syringe barrel 30, as depicted in FIG. 6C. This allows the needle 240 to be disposed in various positions within the drug delivery device during one or more of assembly, actuation, or use of the drug delivery device.

In addition, in one example, the tube 250 may be coextruded, and the inner layer 252 may include material selected for drug product contact, such as bromobutyl rubber. The outer layer 254 may include material selected for vapor barrier properties. In another example, the outer layer 254 may include a heat-shrink sleeve 255, such as a Teflon heat shrink sleeve, as depicted in FIG. 6D. Said another way, applying a Teflon heat-shrink sleeve to an outside surface of an inner layer of the tubing is one way of creating two layers of the tube.

The tube 250 may further comprise one or more of at least one coil 256 or a spring-like portion 258 having a proximal end 260 adapted to be coupled to the syringe barrel 30 and a distal end 262 adapted to be coupled to the needle assembly 236. In one example, the at least one coil 256 or the spring-like portion 258 of the tube 250 of the flexible connection 242 and the needle may again be formed as a single piece construction, with no other connection or coupling member needed between any coil 256 or spring-like portion 258 and the needle assembly 236 or needle 240. So constructed, the at least one coil 256 enables the rigid material of the needle 240 to function as a flexible material. Said another way, the coils 256 in the single piece construction, for example, allow the needle 240 to be flexible. In addition, the at least one coil 256 may help reduce strain in the material of the tube 250 during assembly and/or actuation, for example. In the filling position depicted in FIG. 6A, the at least one coil 256 and the spring-like portion 258 are in a compressed state. As depicted in FIGS. 6B and 6C, the at least one coil 256 and the spring-like portion 258 are in an extended state in one or more of the assembled position or the actuated position. In addition, the tube 250 may include one or more of a shape memory alloy, stainless steel, or nitinol. Alternatively, the flexible connection 242 may include a flexible tube having only a single layer. In this example, the flexible tube may comprise stainless steel.

Further, as depicted in FIGS. 6A and 6B, the needle 240, the flexible connection 242, and the syringe barrel 30 may be coaxial in one or more of the filling position, as depicted in FIG. 6A, or the assembled and the actuated positions of FIG. 6B. Alternatively, the flexible connection 242 and the syringe barrel 30 may be non-coaxial in one or more of the assembled position or the actuated position, as depicted in FIG. 6C. In a similar manner, the longitudinal axis of the needle 240 may be perpendicular to the longitudinal axis of the syringe barrel 30 in one or more of the assembled position or the actuated position, as depicted in FIG. 6C.

Alternatively, the flexible connection 242 may not include any coil or spring-like portion and still accomplish the non-coaxial configuration of FIG. 6C. For example, the flexible connection 242 may include a superelastic alloy, such as nitinol, and still operate in the manner described above relative to FIG. 6C, for example. Still further, in other examples, the tube may include a first portion extending from the proximal end of the tube past at least a mid-point of the tube. The first portion may have an inner diameter that is larger than, such as at least 25 percent larger than, an inner diameter of a second portion of the tube extending from the distal end of the tube. So configured, the flow restriction caused by additional needle length is reduced.

In view of the foregoing, one of ordinary skill in the art will appreciate the following example method 100 of assembling the drug delivery device 10 having the new syringe assembly 12, 112, 212. More specifically, the method 100 includes maintaining a filling position of the syringe assembly 12, 112, 212 during a processing state, the filling position a position in which a longitudinal axis B of the needle assembly 36, 136, 236 of the syringe assembly 12, 112, 212 is parallel to a longitudinal axis A of a syringe barrel 30 of the syringe assembly 12, 112, 212. In addition, the method 100 may further include moving the needle assembly 36, 136, 236 from the filling position to an assembled position within the drug delivery device 10 by the flexible connection 42, 142, 242, the flexible connection 42, 142, 242, disposed between and coupled to the syringe barrel 30 and the needle assembly 36, 136, 236. The assembled position is a position in which the longitudinal axis B of the needle assembly 36, 136, 236 is not parallel to the longitudinal axis A of the syringe barrel 30.

In another example, the method 100 may further include filling the syringe barrel 30 of the syringe assembly 12, 112, 212 with medicament in the filling position of the processing state. In yet another example, the method 100 may further include disposing the syringe assembly 12, 112, 212 into the housing 14 of the drug delivery device 10. In some examples, the syringe assembly 12, 112, 212 may be first disposed within the housing 14 and then the needle assembly 36 is moved from the filling position to the assembled position once disposed within the housing 14 of the drug delivery device 10. In other examples, the syringe assembly 12, 112, 212 may be disposed within the housing 14 of the drug delivery device 10 after the needle assembly 36, 136, 236, is moved from the filling position to the assembled position.

In one example, maintaining a filling position of the syringe assembly 12, 112, 212 during a processing state may comprise maintaining a filling position of the syringe assembly 12 by a rigid connection 60 separate from the flexible connection 42, the rigid connection 60 having a proximal portion 62 coupled to a distal end 34 of the syringe barrel 30 and a distal portion 64 coupled to a needle hub 38 of the needle assembly 36.

In yet another example, moving the needle assembly 36, 136, 236 from the filling position to an assembled position by a flexible connection 42, 142, 242 comprises moving the flexible connection 42, 142, 242 disposed between the syringe barrel 30 and the needle hub 38 or needle assembly 136, 236 such that the needle assembly 36, the flexible connection 42, and the syringe barrel 30 are non-coaxial. In yet another example, moving the needle assembly 36, 136, 236 from the filling position to the assembled position by the flexible connection 42, 142, 242 comprises moving the needle assembly 36, 136, 236 to a position perpendicular to a longitudinal axis A of the syringe barrel 30. In this way, the longitudinal axis B of the needle assembly 36, 136, 236 is perpendicular to the longitudinal axis A of the syringe barrel 30.

In still another example, the method 100 may further comprise forming a fluid pathway 47 between the syringe barrel 30 and the needle assembly 36 by the flexible connection 42.

Still further, the method 100 may further comprise maintaining alignment of the needle assembly 36 with the syringe barrel 30 in the filling position by a rigid connection 60 disposed between the needle assembly 36 and the syringe barrel 30 and separate from the flexible connection 42.

In view of the foregoing, one of ordinary skill in the art will appreciate the many advantages of the new syringe assembly 12, 112, 212 the drug delivery device 10 and methods of present disclosure. For example, the flexible connection 42, 142, 242 of the new syringe assembly 12 enables the needle assembly 36, 136, 236 and the syringe barrel 30 to be handled as a linear assembly during the filling process, but have an angle between the needle assembly 36, 136, 236 and the syringe barrel 30 when assembled into the drug delivery device. Because the angle the needle assembly 36, 136, 236 may be disposed relative to a longitudinal axis A of the syringe barrel 30 may be any one of greater than 0 degrees and less than 180 degrees, the syringe assembly 12, 112, 212 is extremely flexible during assembly. This allows the syringe assembly 12, 112, 212 to be used with many different shapes and designs of various drug delivery devices after processing and/or filling. In addition, having the syringe assembly 12, 112, 212 with the needle 40, 140, 240 allows for still other new and ergonomic drug delivery device designs to be created and implemented. In addition, the new syringe assembly 12, 112, 212 prevents subtle asymmetry during existing syringe filling and inspection processes, for which many existing syringe designs were unfeasible and/or would require redesign of existing processing equipment. Thus, the new syringe assembly 12, 112, 212 allows existing processing equipment to still be used. The new syringe assembly 12, 112, 212 allows for the needle 40, 140 to be disposed perpendicular to the longitudinal axis A of the syringe barrel 30, allowing the syringe assembly 12, 112, 212 to be used with drug delivery devices requiring a needle to be disposed at a 90 degree angle.

Still further, the syringe assembly 12, 112, 212 is able to be disposed within many drug delivery devices, such as the drug delivery device 10 of the present disclosure, which hides the needle assembly 36, 136, 236 for providing a more comfortable grip and a less intimidating appearance when compared to convention medicinal syringes. As a result, the drug delivery devices using the syringe assembly 12, 112, 212, for example, can help decrease potential patient anxiety, thereby increasing compliance and patient satisfaction. Of course, the foregoing advantages are representative advantages only; one of ordinary skill in the art will appreciate that the scope of the present disclosure is not limited to these or any other benefits and advantages described herein, and other benefits and advantages may result from the disclosed embodiments and any modifications thereto in accordance with principles of the present disclosure.

The above description describes various systems and methods for use with the new syringe assembly of the drug delivery device. It should be clear that the syringe assembly, the drug delivery device or methods can further comprise use of a medicament listed below with the caveat that the following list should neither be considered to be all inclusive nor limiting. The medicament will be contained in one or more of a reservoir or a syringe barrel of a pre-filled syringe. In some instances, the reservoir is a primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgrastim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4 (N), Con4 (N) 1K WT; 2xCon4 (N) 1K; L1C; L1C 1K; 2xL1C; Con4C; Con4C 1K; 2xCon4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AblA1; AbIF; AbIK, AbIP; and AbIP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA ($\gamma$4), deposited at the ATCC under number PTA-5214, and a light chain encoded by a polynucleotide in plasmid 15H12/19D12 LCF ($\kappa$), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4ß7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgrastim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFß mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223, 593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, bispecific T cell engager (BiTE®) antibodies, e.g. BLINCYTO® (blinatumomab), can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the drug delivery device, the syringe assembly, methods, and elements thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention.

It should be understood that the legal scope of the invention is defined by the words of the claims set forth at the end of this patent. The appended claims should be construed broadly to include other variants and embodiments of same, which may be made by those skilled in the art without departing from the scope and range of equivalents of the drug delivery device, the syringe assembly and methods.

It should be understood that the legal scope of the invention is defined by the words of the claims set forth at the end of this patent. The appended claims should be construed broadly to include other variants and embodiments of same, which may be made by those skilled in the art without departing from the scope and range of equivalents of the devices, systems, methods, and their elements.

What is claimed is:

1. A drug delivery device comprising:
a housing having an actuating mechanism; and
a syringe assembly disposed within the housing and operatively coupled to the actuating mechanism, the syringe assembly including:
a syringe barrel having a proximal end, a distal end, and a longitudinal axis;
a needle assembly operatively coupled to the syringe barrel, the needle assembly having a needle; and
a flexible connection disposed between the syringe barrel and the needle assembly, the flexible connection comprising one of: (1) a proximal end coupled to the syringe barrel, a distal end coupled to the needle assembly, and a rigid connection separate from the flexible connection and having a proximal leg and a distal leg, the proximal leg directly coupled to the distal end of the syringe barrel or (2) a tube having one or more of at least one coil or a spring-like portion having a distal end adapted to be coupled to or formed with the needle assembly and a proximal end adapted to be directly coupled to the syringe barrel;
wherein the flexible connection enables the needle assembly to be moveable from a filling position, in which a longitudinal axis of the needle assembly is generally parallel to the longitudinal axis of the syringe barrel, to one or more of an assembled position or an actuated position, in which the longitudinal axis of the needle is not generally parallel to the longitudinal axis of the syringe barrel, allowing the needle to be disposed in various positions within the housing during one or more of assembly, actuation, or use of the drug delivery device.

2. The drug delivery device of claim 1, wherein the needle assembly further comprises a needle hub attached to the needle and the needle is stationary relative to the needle hub.

3. The drug delivery device of claim 2, the rigid connection having a proximal portion coupled to the distal end of the syringe barrel and a distal portion coupled to the needle hub.

4. The drug delivery device of claim 3, wherein the rigid connection further includes a body having the proximal leg and the distal leg, the proximal leg downwardly and outwardly extending from the body and the distal leg downwardly and outwardly extending from the body.

5. The drug delivery device of claim 1, wherein the needle, the flexible connection, and the syringe barrel are coaxial in the filling position.

6. The drug delivery device of claim 1, wherein the longitudinal axis of the needle assembly is disposed at an angle that is not generally parallel to the longitudinal axis of the syringe barrel in one or more of the assembled position or the actuated position.

7. The drug delivery device of claim 1, wherein the flexible connection includes a width that is one or more of substantially the same or less than a width of the syringe barrel and a length that is less than a length of the syringe barrel, the flexible connection being moveable at any point along the length or the width of the flexible connection.

8. The drug delivery device of claim 1, wherein the flexible connection comprises the tube, and the tube comprises at least two layers including an inner layer and an outer layer, the inner layer including material selected for drug product contact, and the outer layer including material selected for vapor barrier properties.

9. A syringe assembly for a drug delivery device, the syringe assembly comprising:
a syringe barrel having a longitudinal axis;
a needle assembly operatively coupled to the syringe barrel, the needle assembly having a needle;
a flexible connection disposed between the syringe barrel and the needle assembly, the flexible connection comprising one of: (1) a proximal end coupled to the syringe barrel, a distal end coupled to the needle assembly, and a rigid connection separate from the flexible connection and having a proximal leg and a distal leg, the proximal leg directly coupled to a distal end of the syringe barrel or 2) a tube having one or more of at least one coil or a spring-like portion having a distal end adapted to be coupled to or formed with the needle assembly and a proximal end adapted to be directly coupled to the syringe barrel;
wherein the flexible connection enables the needle assembly to be moveable from a filling position to one or more of an assembled position or an actuated position, the filling position a position in which a longitudinal axis of the needle assembly is generally parallel to a longitudinal axis of the syringe barrel, and the assembled position and the actuated position are positions in which the longitudinal axis of the needle assembly is not generally parallel to the longitudinal axis of the syringe barrel, allowing the needle to be disposed in various positions within the drug delivery device during one or more of assembly, actuation, or use of the drug delivery device.

10. The syringe assembly of claim 9, wherein the needle, the flexible connection, and the syringe barrel are coaxial in the filling position.

11. The syringe assembly of claim 9, wherein the longitudinal axis of the needle assembly is disposed at an angle that is not generally parallel to the longitudinal axis of the syringe barrel in one or more of the assembled position or the actuated position.

12. The syringe assembly of claim 9, wherein the flexible connection includes a width that is one or more of substantially the same or less than a width of the syringe barrel and a length that is less than a length of the syringe barrel, the flexible connection being moveable at any point along the length or the width of the flexible connection, forming a fluid pathway between the syringe barrel and the needle, and allowing movement of the needle without movement of the syringe barrel.

13. The syringe assembly of claim 9, wherein the flexible connection comprises the rigid connection, the rigid connection for preventing movement of the flexible connection in the filling position and having a proximal portion coupled to the syringe barrel and a distal portion coupled to a needle hub.

14. The syringe assembly of claim 13, wherein the rigid connection further includes a body having the proximal leg and the distal leg, the proximal leg downwardly and outwardly extending from the body and the distal leg downwardly and outwardly extending from the body.

15. The syringe assembly of claim 9, wherein the flexible connection comprises the tube, and the tube comprises at least two layers including an inner layer and an outer layer, the inner layer including material selected for drug product contact, and the outer layer including material selected for vapor barrier properties.

* * * * *